United States Patent
Rajaiah et al.

(10) Patent No.: US 6,491,896 B1
(45) Date of Patent: Dec. 10, 2002

(54) POLYBUTENE CONTAINING DENTURE CLEANSER COMPOSITIONS

(75) Inventors: Jayanth Rajaiah, Loveland, OH (US); Lisa Catron Ernst, Cincinnati, OH (US); Ann Maria Case, Cincinnati, OH (US); Thinh Nguyen Ha, Cincinnati, OH (US); William Michael Glandorf, Mason, OH (US); Christopher Robert Mayer, Cincinnati, OH (US)

(73) Assignee: The Proctor & Gamble Company, Cincinnati, OH (US)

( * ) Notice: Subject to any disclaimer, the term of this patent is extended or adjusted under 35 U.S.C. 154(b) by 0 days.

(21) Appl. No.: 10/084,870

(22) Filed: Feb. 28, 2002

Related U.S. Application Data

(60) Provisional application No. 60/276,976, filed on Mar. 19, 2001.

(51) Int. Cl.[7] .............................. A61K 9/46; C11D 7/18; C11D 7/54; C11Q 17/00
(52) U.S. Cl. .......................................... 424/44; 510/117
(58) Field of Search ............................................. 424/44

(56) References Cited

U.S. PATENT DOCUMENTS

| | | | | |
|---|---|---|---|---|
| 3,974,293 A | * | 8/1976 | Witzel | 426/4 |
| 4,061,780 A | * | 12/1977 | Yoshida et al. | 424/358 |
| 4,108,823 A | | 8/1978 | Yoshimura et al. | |
| 4,158,543 A | * | 6/1979 | Orlowski | 8/137 |
| 4,495,314 A | | 1/1985 | Keegan | |
| 4,555,154 A | | 11/1985 | White | |
| 4,613,646 A | * | 9/1986 | Sandvick | 524/476 |
| 4,810,407 A | * | 3/1989 | Sandvick | 252/90 |
| 4,975,270 A | * | 12/1990 | Kehoe | 424/48 |
| 5,051,130 A | * | 9/1991 | Futami et al. | 106/35 |
| 5,114,718 A | | 5/1992 | Damani | |
| 5,185,386 A | | 2/1993 | Cohen et al. | |
| 5,204,390 A | * | 4/1993 | Szymanski et al. | 524/91 |
| 5,449,473 A | * | 9/1995 | Bunczk et al. | 252/104 |
| 5,496,541 A | | 3/1996 | Cutler | |
| 5,543,443 A | | 8/1996 | Rajaiah et al. | |
| 5,648,326 A | * | 7/1997 | Sramek | 510/284 |
| 5,652,208 A | * | 7/1997 | Sramek | 510/284 |
| 5,656,286 A | * | 8/1997 | Miranda et al. | 424/449 |
| 5,709,873 A | * | 1/1998 | Barshalom et al. | 424/49 |
| 5,888,602 A | * | 3/1999 | Davis et al. | 428/40.1 |
| 5,900,230 A | | 5/1999 | Cutler | |
| 5,965,255 A | * | 10/1999 | Ichimura et al. | 428/353 |
| 6,069,188 A | | 5/2000 | Rajaiah et al. | |
| 6,103,266 A | * | 8/2000 | Tapolsky et al. | 424/484 |
| 6,112,477 A | * | 9/2000 | Spinks | 52/172 |
| 6,139,865 A | * | 10/2000 | Friend et al. | 424/441 |
| 6,194,364 B1 | * | 2/2001 | Glenn | 510/130 |
| 6,197,288 B1 | * | 3/2001 | Mankou | 424/49 |
| 6,331,533 B1 | * | 12/2001 | Harvey et al. | 424/47 |

FOREIGN PATENT DOCUMENTS

| | | |
|---|---|---|
| CA | 2031121 | 6/1991 |
| DE | 25 58 602 A1 | 6/1977 |
| DE | 25 58 602 B2 | 3/1979 |
| DE | 25 58 602 C3 | 6/1997 |
| JP | 57-059529 | 4/1982 |
| JP | Hei 4-149110 | 5/1992 |
| JP | 9-012419 | 1/1997 |
| JP | 12-126206 | 5/2000 |

OTHER PUBLICATIONS

Nitto Kagaku KK JP. 09279190A Polybutene M.W. 500–3,000 + polyisobutyles M.W. 10,000–600,000 cleans stain on coating films, glasses, plastics + castor oil castor oil makes it less sticky, Oct. 1997.*

Nippon Oils & Fats JP 75016365B light weight low molecular weight polybutene, surfactants and ink cleans oily stains, Jun. 1975.*

* cited by examiner

Primary Examiner—Shep K. Rose
(74) Attorney, Agent, or Firm—Andrea L. Winslow

(57) ABSTRACT

A denture cleanser composition comprising polybutene, with a molecular weight of about 300 to about 3000, an effervescence generator and a bleaching agent. Optionally, denture cleanser compositions may further comprise tablet binders, organic peroxyacid bleach precursors, surfactants including a dimethicone copolyol, lipophilic compounds such as flavorants and coolants, chelating agents, and other therapeutic and cosmetic active agents.

23 Claims, No Drawings

POLYBUTENE CONTAINING DENTURE CLEANSER COMPOSITIONS

CROSS-REFERENCE TO RELATED APPLICATIONS

This application claims the benefit of U.S. Provisional Application No. 60/276,976, filed Mar. 19, 2001.

FIELD OF THE INVENTION

The present invention relates to a cleanser composition that is especially useful for cleansing dentures and the like. In particular, the present invention relates to denture cleansing compositions having enhanced anti-plaque activity together with excellent denture cleansing performance, which may be used to deliver additional therapeutic and cosmetic benefits.

BACKGROUND OF THE INVENTION

Effervescent tablets and powders for cleansing dentures are well known in the art. The aim of a denture cleanser product is to clean the denture as fully and as quickly as possible to remove the accumulation of plaque, mucilaginous and bacterial deposits which collect while the denture is being worn. To wear a denture, which has not been completely cleaned of plaque and bacterial deposits, is not only unhygienic but can also, within a short time, result in detrimental effects to the mucous membrane. Moreover, bacterial deposits can lead to so-called bacterial corrosion of the plastics material used to produce the denture with consequent color change and malodor formation. Conventional denture cleansers typically do not maintain actives in the oral cavity long enough to optimally enhance or prolong the therapeutic, prophylactic and/or cosmetic benefits provided by the actives. In order to provide a denture cleanser with sufficient substantivity to provide sustained release of a denture cleansing agent and optionally additional denture care actives, the use of polybutene in a denture cleanser composition is herein disclosed.

Polybutene is recognized as a component of denture adhesives and as a gum base. U.S. Pat. No. 5,880,172, issued Mar. 3, 1999, to Rajaiah, et al., discloses a self-supporting denture adhesive that is peelable for easy removal, which incorporates polybutene as an optional ingredient. U.S. Pat. No. 5,496,541, issued Mar. 5, 1996, to Cutler, relates to a dentifrice chewing gum and teaches the use of polybutene as an optional gum base. Such known applications often employ a higher molecular weight polybutene in order to achieve the desired results.

In the present invention lower molecular weight polybutene is incorporated in the denture cleanser composition to provide a protective coating on the artificial teeth. The lower molecular weight polybutene is a flowable liquid that achieves good coating of the denture and is extremely substantive. Sustained release of the denture cleansing active agent is achieved. Through sustained release of additional denture care actives optionally incorporated in the present invention the denture surface receives optimal therapeutic and cosmetic benefits.

The present invention provides a denture cleanser composition that effectively cleanses dentures, dental plates, and other hard surfaces temporarily fixed within the oral cavity and provides a coating to the same surfaces thereby preventing the buildup of plaque and other debris. The coating inhibits and prevents staining of the denture. This coating also provides a slick, smooth feel to the denture surface, which consumers view as an indicator of clean teeth. The coating may also provide sustained release of other denture care actives and ingredients.

SUMMARY OF THE INVENTION

The present invention relates to a denture cleanser composition comprising polybutene with a molecular weight of about 300 to about 3000; an inorganic persalt bleaching agent; and an effervescence generator. Additional components may be added to the present invention including, without limitation, an organic peroxyacid bleach precursor, lipophilic compounds, dental abrasives, binders, humectants, surfactants, chelating agents and other denture care actives.

DETAILED DESCRIPTION OF THE INVENTION

The denture cleanser compositions of the invention comprise polybutene, an effervescence generator and an inorganic persalt bleaching agent. In one embodiment, these essential components are supplemented by additional components, which may include an organic peroxyacid bleach precursor, lipophilic compounds, dental abrasives, binders, humectants, surfactants, chelating agents, and other cosmetic and therapeutic denture care actives. Each of these will be discussed in turn.

Definitions

The terms "artificial teeth" and "dentures", as used herein, are meant to include dentures, dental plates, bridges and other hard surfaces of dental appliances which are temporarily fixed within the oral cavity and which are typically removed from the oral cavity for cleaning.

By "safe and effective amount", as used herein, is meant an amount of an agent (e.g., anti-calculus agent) high enough to significantly improve the condition to be treated, but low enough to avoid serious side effects (at a reasonable benefit/risk ratio), within the scope of sound medical/dental judgment. The safe and effective amount of an agent (e.g., anti-calculus agent) may vary with the particular condition being treated, the age and physical condition of the patient being treated, the severity of the condition, the duration of treatment, the nature of concurrent therapy, the specific form of the source employed, and the particular vehicle from which the agent is applied.

The term "non-self supporting" is used to describe a composition that lacks integrity and strength. In the instant case, this means that the composition is unable to be detached as one solid piece from the teeth even after several hours of use in the mouth. The composition cannot be cut and formed into definite shapes, such as a sheet or cone, which maintain their initial dimensions.

The term "mucoadhesive" or "bioadhesive" as used herein refers to the phenomenon where a natural or synthetic substance applied to a wet mucosal epithelium adheres, usually creating a new interface, to the mucous layer. (*CRC Critical Review in Ther Drug Carrier*, Vol.5, Issue 1, p.21 (1988)). Generally, mucoadhesion can be achieved via physical or chemical processes, or both. This mechanism is described in *Journal of Controlled Release*, Vol.2, p257 (1982) and *Journal of Controlled Release*, Vol.18 (1992) p. 249. The above references are incorporated by reference herein in their entirety.

Herein, the terms "tartar" and "calculus" are used interchangeably and refer to mineralized dental plaque biofilms.

The term "unit dose form" refers to physically discrete units suitable as unitary dosages for human subjects and other mammals, each containing a predetermined quantity of active material calculated to produce the desired therapeutic effect.

The term "viscosity" as used herein refers to kinematic viscosity, measured using the standard test method for Kinematic Viscosity of Transparent and Opaque Liquids (the Calculation of Dynamic Viscosity), ASTM D-445. As reported, viscosity is measured at 99° C. (210° F.) unless otherwise indicated. A sample is placed in a U-shaped "Cannon-Fenske" type viscometer (for transparent liquids) tube and submerged into a constant temperature bath. Flow is timed between two marks on the tube and viscosity is determined by simple calculations dependent on time and a standard factor supplied by the tube manufacturer.

"Molecular weight", as referred to herein, is reported as a number average, determined using gel permeation chromatography. The number average molecular weight, or arithmetic mean, is a function of the number of molecules in a given mass of polymer. It is represented by the formula:

$$M_n = \frac{\sum N_i M_i}{\sum N_i} = \sum n_i M_i$$

where $N_i$, represents the number of molecules present for a given molecular weight, $M_i$ and $n_i=N_i/\Sigma N_i$ is the number fraction of molecular weight, $M_i$.

Percentages and ratios herein are by weight of total composition, unless otherwise indicated.

Polybutene

Polybutene is a viscous copolymer of isobutylene and butene monomers. "Polybutene", as used herein, refers to both hydrogenated (CAS #68937-10-0) and unhydrogenated (CAS #9003-29-6) forms of the polymer. Polybutene is a viscous, colorless, non-drying, liquid polymer. Forms of polybutenes range from a flowable liquid to a near semi-solid state. Polybutenes are clear, odorless, chemically stable, resistant to oxidation by light and heat, non-toxic and non-hazardous.

The composition of the present invention comprises polybutene, generally of a lower molecular weight from about 300 to about 3000, in another embodiment from about 500 to about 2200, and in another embodiment from about 750 to about 1500. The viscosity of the polybutene disclosed herein, ranges from about 30 cSt (centi Stoke) measured at 38° C. to about 4,500 cSt measured at 99° C., in another embodiment from about 200 cSt measured at 38° C. to about 3,500 cSt measured at 99° C. and in another embodiment from about 75 cSt measured at 99° C. to about 700 cSt measured at 99° C. Polybutene comprises from about 0.01% to about 100%, in another embodiment from about 1% to about 100%, in yet another embodiment from about 50% to about 100% by weight of the composition.

The lower molecular weight polybutene of the present invention does not exhibit elastomeric properties. Elastomers are amorphous polymers that have the ability to stretch out and spring back to their original shapes. Such elastomeric polymers must have a modest amount of cross-linking to prevent the polymeric chains from slipping over one another, and the chains must have an irregular shape to prevent the formation of crystalline regions within the polymeric chains. Synthetic elastomers, are described in more detail in Kirk-Othmer, *Encyclopedia of Chemical Technology*, Fourth Edition, Volume 8, Wiley-Interscience Publishers (1996), pages 934–955, incorporated herein by reference in its entirety, including all references incorporated into Kirk-Othmer. The polybutene of the present invention is not cross-linked and does not exhibit rubbery or elastic behavior. When subjected to a stretching or bending force, the polybutene of the present invention does not return to its original shape upon the removal of the force.

Lower molecular weight polybutene (Molecular Weight= 300–3000), which is a flowable liquid known for its adhesive properties, is actually non-mucoadhesive. That is, the polybutene, while displaying excellent adhesion properties on the hard surfaces of the oral cavity, will not significantly adhere to the mucosa or wet, soft tissue of the mouth. Therefore, polybutene is extremely substantive when applied to the denture, making it suitable for once daily application and treatment. High retention of the polybutene is achieved, even when thorough brushing has occurred. Thus, the polybutene, once applied to the denture surface, is long lasting, and rinse resistant, which allows for sustained release of certain optional denture care actives. Importantly, the compositions of the present invention are not self-supporting neither before, during, nor after application to the artificial teeth.

Once applied to the denture, the polybutene has a very smooth, slick texture, perceived by the consumer as a desirable, clean feeling. The polybutene acts as a lubricant and reduces the friction normally produced when the tongue slides over these surfaces.

Suitable polybutenes for use herein include, but are not limited to: Indopol L-14, Molecular Weight ("MW")=370; Indopol L-50, MW=455; Indopol L-65, MW=435; Indopol L-100, MW=510, H-15, MW=600; H-25, MW=670; H-35, MW=725; H-40, MW=750; H-50, MW=815; H-100, MW=940; H-300, MW=1330; H-1500, MW=2145; H-1900, MW=2270; Panalane L-14E, MW=370; Panalane H-300E, MW=1330; all trade names of BP Amoco Chemicals (Chicago, Ill.). Other suitable grades of polybutene include Parapol 450, MW=420; Parapol 700, MW=700; Parapol 950, MW=950; Parapol 1300, MW=1300; and Parapol 2500, MW=2700; all trade names of ExxonMobil Corporation.

Inorganic Persalt Bleaching Agent

Another essential element of the composition of the present invention is a bleaching agent. Typically the bleaching agent takes the form of an inorganic persalt and can be selected from any of the well-known bleaching agents known for use in denture cleansers such as the alkali metal and ammonium persulfates, perborates, percarbonates and perphosphates and the alkali metal and alkaline earth metal peroxides. Examples of suitable bleaching agents include potassium, ammonium, sodium and lithium persulfates and perborate mono- and tetrahydrates, sodium pyrophosphate peroxyhydrate and magnesium, calcium, strontium and zinc peroxides. Of these, however, the alkali metal persulfates, perborates and mixtures thereof are preferred for use herein. In one embodiment the inorganic persalt bleaching agent is selected from the alkali metal perborates. Indeed, it is a feature of the invention that the tablet compositions herein will provide excellent antimicrobial activity even in the absence of alkali metal persulfates.

The amount of bleaching agent in the total composition is generally from about 5 to about 70% preferably from about 10% to about 50%. In compositions comprising a mixture of alkali metal persulfates and perborates, the overall persulfate:perborate ratio is suitably from about 5:1 to about 1:5, more especially from about 2:1 to about 1:2.

Effervesence Generator

The denture cleansing compositions also comprise an effervescence generator, i.e. a material that, in the presence of water, releases carbon dioxide or oxygen with effervescence. The effervescence generator can be selected from generators which are effective under acid, neutral or alkaline pH conditions, but preferably it consists of a combination of a generator which is effective or most effective under acid or neutral pH conditions and a generator which is effective or most effective under alkaline pH conditions. Effervescence generators which are effective under acid or neutral pH conditions include a combination of at least one alkali metal carbonate or bicarbonate, such as sodium bicarbonate, sodium carbonate, sodium sesquicarbonate, potassium carbonate, potassium bicarbonate, or mixtures thereof, in admixture with at least one non-toxic, physiologically-acceptable organic acid, such as tartaric, fumaric, citric, malic, maleic, gluconic, succinic, salicylic, adipic or sulphamic acid, sodium fumarate, sodium or potassium acid phosphates, betaine hydrochloride or mixtures thereof. Of these, malic acid is preferred. Effervescence generators which are effective under alkaline pH conditions include persalts such as alkali and alkaline earth metal peroxoborates as well as perborates, persulphates, percarbonates, perphosphates, and mixtures thereof as previously described. For example, a mixture of an alkali metal perborate (anhydrous, mono-, or tetrahydrate) with a monopersulphate such as Caroat©, marketed by E I du Point de Nemours Co., which is a 2:1:1 mixture of monopersulphate, potassium sulphate and potassium bisulphate and which has an active oxygen content of about 4.5%, is suitable for use herein.

In one embodiment denture cleansing compositions in tablet form, incorporate an effervescence generator that takes the form of a solid base material which in the presence of water releases carbon dioxide or oxygen with effervescence. Suitably, the solid base material incorporates a (bi) carbonate/acid effervescent couple optionally in combination with a perborate/persulphate oxygen effervescence generator. The combination of generators is valuable for achieving optimum dissolution characteristics and pH conditions for achieving optimum cleaning and antimicrobial activity. The (bi)carbonate components generally comprise from about 5% to about 65%, preferably from about 25% to 55% of the total composition. The acid components generally comprise from about 5% to about 50%, preferably from about 10% to about 30% of the total composition.

Optional Ingredients

The denture cleansing compositions of the present invention can be supplemented by other known components of such formulations. Denture cleansing compositions of the invention can be supplemented by other usual components of such formulations, especially organic peroxyacid bleach precursors; lipophilic compounds including flavorants, physiological cooling agents, and perfumes; surfactants; chelating agents; enzymes; dyestuffs; sweeteners; tablet binders and fillers; foam depressants such as dimethylpolysiloxanes; foam stabilizers such as the fatty acid sugar esters; preservatives; lubricants such as talc, magnesium stearate, finely divided amorphous pyrogenic silicas, etc.; and additional therapeutic and cosmetic active agents. The free moisture content of the final composition is desirably less than about 1% and especially less than about 0.5%.

Tablet Binders and Fillers

Tablet binders and fillers suitable for use herein include polyvinyl-pyrrolidone, poly (oxyethylene) of molecular weight 20,000 to 500,000, polyethyleneglycols of molecular weight of from about 1000 to about 50,000, Carbowax having a molecular weight of from 4000 to 20,000, nonionic surfactants, fatty acids, sodium carboxymethyl cellulose, gelatin, fatty alcohols, clays, polymeric polycarboxylates, sodium carbonate, calcium carbonate, calcium hydroxide, magnesium oxide, magnesium hydroxide carbonate, sodium sulfate, proteins, cellulose ethers, cellulose esters, polyvinyl alcohol, alginic acid esters, vegetable fatty materials of a pseudocolloidal character. Of the above, polyethyleneglycols are highly preferred, especially those having molecular weight of from about 1,000 to about 30,000, preferably from about 12,000 to about 30,000.

Organic Peroxyacid Bleach Precursors

In one embodiment the present invention further comprises an organic peroxyacid precursor, which in general terms can be defined as a compound having a titre of at least 1.5 ml of 0.1N sodium thiosulfate in the following peracid formation test.

A test solution is prepared by dissolving the following materials in 1000 mls distilled water:

| | |
|---|---|
| sodium pyrophosphate ($Na_4P_2O_7.10H_2O$) | 2.5 g |
| Sodium perborate ($NaBO_2.H_2O_2.3H_2O$) having 10.4% available oxygen | 0.615 g |
| sodium dodecylbenzene sulphonate | 0.5 g |

To this solution at 60° C. an amount of activator is added such that for each atom of available oxygen present one molecular equivalent of activator is introduced. The mixture obtained by addition of the activator is vigorously stirred and maintained at 60° C. After 5 minutes from addition, a 100 ml portion of the solution is withdrawn and immediately pipetted onto a mixture of 250 g cracked ice and 15 ml glacial acetic acid. Potassium iodide (0.4 g) is then added and the liberated iodine is immediately titrated with 0.1 N sodium thiosulphate with starch as indicator until the first disappearance of the blue colour. The amount of sodium thiosulphate solution used in ml is the titre of the bleach activator.

The organic peracid precursors are typically compounds containing one or more acyl groups, which are susceptible to perhydrolysis. The preferred activators are those of the N-acyl or O-acyl compound type containing an acyl radical R—CO wherein R is a hydrocarbon or substituted hydrocarbon group having preferably from about 1 to about 20 carbon atoms. Examples of suitable peracid precursors include:

1) Acyl organoamides of the formula $RCONR_1R_2$, where RCO is carboxylic acyl radical, $R_1$ is an acyl radical and $R_2$ is an organic radical, as disclosed in U.S. Pat. No. 3,117,148. Examples of compounds falling under this group include:
   a) N,N-diacetylaniline and N-acetylphthalimide;
   b) N-acylhydantoins, such as N,N'-diacetyl-5,5-dimethylhydantoin;
   c) Polyacylated alkylene diamines, such as N,N,N'N'-tetraacetylethylenediamine (TAED) and the corresponding hexamethylenediamine (TAHD) derivatives, as disclosed in GB-A-907,356, GB-A-907,357 and GB-A-907,358;
   d) Acylated glycolurils, such as tetraacetylglycoluril, as disclosed in GB-A-1,246,338, GB-A-1,246,339 and GB-A-1,247,429.

2) Acylated sulphonamides, such as N-methyl-N-benzoyl-menthane sulphonamide and N-phenyl-N-acetyl menthane sulphonamide, as disclosed in GB-A-3,183,266.

3) Carboxylic esters as disclosed in GB-A-836,988, GB-A-963,135 and GB-A-1,147,871. Examples of compounds of this type include phenyl acetate, sodium acetoxy benzene sulphonate, trichloroethylacetate, sorbitol hexaacetate, fructose pentaacetate, p-nitrobenzaldehyde diacetate, isopropeneyl acetate, acetyl aceto hydroxamic acid, and acetyl salicylic acid. Other examples are esters of a phenol or substituted phenol with an alpha-chlorinated lower aliphatic carboxylic acid, such as chloroacetylphenol and chloroacetylsalicylic acid, as disclosed in U.S. Pat. No. 3,130,165.

4) Carboxylic esters having the general formula AcL wherein Ac is the acyl moiety of an organic carboxylic acid comprising an optionally substituted, linear or branched $C_6$–$C_{20}$ alkyl or alkenyl moiety or a $C_6$–$C_{20}$ alkyl-substituted aryl moiety and L is a leaving group, the conjugate acid of which has a pKa in the range from 4 to 13, for example oxybenzenesulfonate or oxybenzoate. Preferred compounds of this type are those wherein:

a) Ac is $R_3$—CO and $R_3$ is a linear or branched alkyl group containing from 6 to 20, in one embodiment 6 to 12, in another embodiment 7 to 9 carbon atoms and wherein the longest linear alkyl chain extending from and including the carbonyl carbon contains from 5 to 18, in one embodiment 5 to 10 carbon atoms, $R_3$ optionally being substituted (preferably alpha to the carbonyl moiety) by Cl, Br, OCH3 or $OC_2H_5$. Examples of this class of material include sodium 3,5,5-trimethylhexanoyloxybenzene sulfonate, sodium 3,5,5-trimethylhexanoyloxybenzoate, sodium 2-ethylhexanoyl oxybenzenesulfonate, sodium nonanoyl oxybenzene sulfonate and sodium octanoyl oxybenezenesulfonate, the acyloxy group in each instance preferably being p-substituted;

b) Ac has the formula $R_3(AO)_m XA$ wherein $R_3$ is a linear or branched alkyl or alkylaryl group containing from 6 to 20, in one embodiment from 6 to 15 carbon atoms in the alkyl moiety, $R_5$ being optionally substituted by Cl, Br, $OCH_3$, or $OC_2H_5$, AO is oxyethylene or oxypropylene, m is from 0 to 100, X is O, $NR_4$ or CO—$NR_4$, and A is CO, CO—CO, $R_6$—CO, CO—$R_6$—CO, or CO—$NR_4$—$R_6$—CO wherein $R_4$ is $C_1$–$C_4$ alkyl and $R_6$ is alkylene, alkenylene, arylene or alkarylene containing from 1 to 8 carbon atoms in the alkylene or alkenylene moiety. Bleach activator compounds of this type include carbonic acid derivatives of the formula $R_3(AO)_m OCOL$, succinic acid derivatives of the formula $R_3OCO(CH_2)_2COL$, glycollic acid derivatives of the formula $R_3OCH_2COL$, hydroxypropionic acid derivatives of the formula $R_3OCH_2CH_2COL$, oxalic acid derivatives of the formula $R_3OCOCOL$, maleic and fumaric acid derivatives of the formula $R_3OCOCH=CHCOL$, acyl aminocaproic acid derivatives of the formula $R_3CONR_1(CH_2)_6COL$, acyl glycine derivatives of the formula $R_3CONR_1CH_2COL$, and amino-6-oxocaproic acid derivatives of the formula $R_3N(R_1)CO(CH_2)_4COL$. In the above, m is in one embodiment from 0 to 10, and R3 is in one embodiment $C_6$–$C_{12}$, in another embodiment $C_6$–$C_{10}$ alkyl when m is zero and $C_9$–$C_{15}$ when m is non-zero. The leaving group L is as defined above.

5) Acyl-cyanurates, such as triacetyl- or tribenzoylcyanurates, as disclosed in U.S. Pat. No. 3,332,882.

6) Optionally substituted anhydrides of benzoic or phthalic acid, for example, benzoic anhydride, m-chlorobenzoic anhydride and phthalic anhydride.

In one embodiment, organic peracid precursors are of types 1(c) and 4(a).

Where present, the level of peroxyacid bleach precursor, by weight of the total composition, is from about 0.1% to about 10%, in one embodiment from about 0.5% to about 5% and is generally added in the form of a bleach precursor agglomerate.

The bleach precursor agglomerates preferred for use herein generally comprise a binder or agglomerating agent, selected from those tablet binders or fillers described above, in a level of from about 5% to about 40%, in one embodiment from about 10% to about 30% by weight thereof.

Preferred from the viewpoint of optimum dissolution and pH characteristics are bleach precursor agglomerates which comprise from about 10% to about 75%, in one embodiment from about 20% to about 60% by weight thereof of peroxyacid bleach precursor, from about 5% to about 60%, in one embodiment from about 5% to about 50%, in another embodiment from about 10% to about 40% of a (bi) carbonate/acid effervescent couple, from about 0% to about 20% of a peroxoboroate, and from about 5% to about 40%, in one embodiment from about 10% to about 30% of an agglomerating agent. The final bleach precursor granules desirably have an average particle size of from about 500 to about 1500, in one embodiment from about 500 to about 1,000 um, this being valuable from the viewpoint of optimum dissolution performance and aesthetics. The level of bleach precursor agglomerates, moreover, is from about 1% to about 20%, in one embodiment from about 5% to about 15% by weight of composition.

Surfactants

Another optional ingredient of the denture cleansing compositions of the invention is a surfactant. The surfactant can be selected from the many available that are compatible with the other ingredients of the denture cleanser, both in the dry state and in solution. Such materials are believed to improve the effectiveness of the other ingredients of the composition by aiding their penetration into the interdental surfaces. Also, these materials aid in the removal of food debris attached to the teeth. Between 0.1% and 5%, by weight of the dry composition of a dry powder or granular anionic surface active agent, such as sodium lauryl sulfate, sodium N-lauroylsarcosinate, sodium lauryl sulfoacetate or dioctyl sodium sulfosuccinate or ricinoleyl sodium sulfosuccinate, may, for example, be included in the composition and in one embodiment the surfactant comprises between 0.5% and 4% of the composition.

Suitable cationic, non-ionic and ampholytic surface active agents include, for example, quaternary ammonium compounds such as cetyltrimethyl-ammonium bromide, condensation products of alkylene oxides such as ethylene or propylene oxide with fatty alcohols, phenols, fatty amines or fatty acid alkanolamides, the fatty acid alkanolamides themselves, esters of long-chained ($C_8$–$C_{22}$) fatty acids with polyalcohols or sugars, for example glycerylmonostearate or saccharose monolaurate or sorbitolpolyoxyethylenemono- or di-stearate, betaines, sulphobetaines or long-chain alkylaminocarboxylic acids.

In one embodiment the surfactant is a silicone surfactant having the general formula (I):

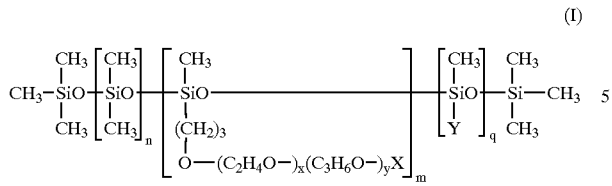

(I)

wherein X is selected from hydrogen, alkyl, alkoxy and acyl groups having from about 1 to about 16 carbon atoms, Y is $CH_3$, q is 0, n is from about 1 to about 100, m is from about 1 to about 40, the molecular weight of the residue $(C_2H_4O-)_x(C_3H_6O-)_yX$ is from about 50 to about 2000, and x and y are such that the weight ratio of oxyethylene:oxypropylene is from about 100:0 to about 0:100.

The silicone surfactant, a dimethicone copolyol, assists in dispersing the polybutene in an aqueous media whilst still allowing the polybutene to deposit onto denture surfaces. In one embodiment, the silicone surfactant is selected from dimethicone copolyols having a HLB value of greater than 14 and mixtures thereof. Highly preferred are end-capped (X is alkyl, more particularly methyl) dimethicone copolyols, especially where the pendant side chain is all oxyethylene (y is 0), such as that marketed under the Trade Name Silwet L7600. The silicone surfactant is generally present in a level of from about 0.01% to about 25%, in one embodiment from about 0.3% to about 10%, in another embodiment from about 0.5% to about 5%, by weight. It will be appreciated that the precise amount will depend on the amount of the polybutene used.

Lipophilic Compounds

The denture cleanser compositions of the present invention may also include a lipophilic compound. In general terms, lipophilic compounds suitable for use herein are oil-like materials which are soluble or solubilisable in the polybutene, typically at a level of at least about 1%, in one embodiment at least about 5%, by weight at 25° C. Preferred lipophilic compounds are selected from flavorants, physiological cooling agents, perfumes and antimicrobial compounds. The polybutene acts to enhance the substantivity of the lipophilic compound to teeth and/or dentures, thereby providing enhanced and/or sustained flavor impact and antimicrobial efficacy.

Lipophilic flavorants suitable for use herein comprise one or more flavor components selected from wintergreen oil, oregano oil, bay leaf oil, peppermint oil, spearmint oil, clove oil, sage oil, sassafras oil, lemon oil, orange oil, anise oil, benzaldehyde, bitter almond oil, camphor, cedar leaf oil, marjoram oil, citronella oil, lavendar oil, mustard oil, pine oil, pine needle oil, rosemary oil, thyme oil, cinnamon leaf oil, and mixtures thereof.

Lipophilic antimicrobial compounds suitable for use herein include thymol, menthol, triclosan, 4-hexylresorcinol, phenol, eucalyptol, benzoic acid, benzoyl peroxide, butyl paraben, methyl paraben, propyl paraben, salicylamides, and mixtures thereof.

The carboxamides found most useful are those described in U.S. Pat. No. 4,136,163, Jan. 23, 1979 to Wason et al., and U.S. Pat. No. 4,230, 688, Oct. 28, 1980 to Rawsell et al.

Physiological cooling agents suitable for use herein include carboxamides, menthane esters, menthane ethers, and mixtures thereof. Suitable menthane ethers for use herein are selected from those with the formula:

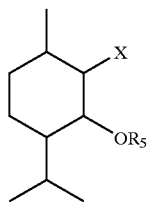

where $R_5$ is an optionally hydroxy substituted aliphatic radical containing up to 25 carbon atoms, preferably up to 5 carbon atoms, and where X is hydrogen or hydroxy, such as those commercially available under the trade name Takasago, from Takasago International Corporation. A particularly preferred cooling agent for use in the compositions of the present invention is Takasago 10 [3-1-menthoxy propan-1,2-diol (MPD)]. MPD is a monoglycerin derivative of 1-menthol and has excellent cooling activity.

The level of lipophilic compound in the compositions of the invention is generally in the range from about 0.001% to about 10%, in one embodiment from about 0.05% to about 5%, in another embodiment from about 0.1% to about 3%, by weight.

Chelating Agents

Chelating agents beneficially aid cleaning and bleach stability by keeping metal ions, such as calcium, magnesium, and heavy metal cations in solution. Examples of suitable chelating agents include sodium tripolyphosphate, sodium acid pyrophosphate, tetrasodium pyrophosphate, aminopoly-carboxylates such as nitrilotriacetic acid and ethylenediamine tetracetic acid and salts thereof, and polyphosphonates and aminopolyphosphonates such as hydroxyethanediphosphonic acid, ethylenediamine tetramethylene-phosphonic acid, diethylenetriaminepentamethylenephosphonic acid and salts thereof. The chelating agent selected is not critical except that it must be compatible with the other ingredients of the denture cleanser when in the dry state and in aqueous solution. Advantageously, the chelating agent comprises between 0.01% and 60%, by weight of the composition, in one embodiment between 0.5% and 30%. Phosphonic acid chelating agents, however, comprise from about 0.001% to about 1%, in one embodiment from about 0.01% to about 0.5%, by weight of composition.

Enzymes

Enzymes suitable for use herein are exemplified by proteases, alkalases, amylases, lipases, dextranases, mutanases, glucanases etc.

Therapeutic and Cosmetic Agents

The denture cleanser compositions of the present invention may further comprise one or more therapeutic or cosmetic active agents selected from the group consisting of anti-calculus agents, fluoride ions sources, stannous ion sources, additional whitening agents, anti-microbial, anti-plaque agents, anti-inflammatory agents, nutrients, antioxidants, anti-viral agents, anti-fungal agents, analgesic and anesthetic agents, H-2 antagonists, components other than polybutene which impart a clean feel to the dentures, pigments, dyes, lakes and colorants, and mixtures thereof. In one embodiment the therapeutic and cosmetic active agents are selected from the group consisting of triclosan, baking soda, sodium fluoride, potassium nitrate, sodium nitrate, nystatin, grapefruit seed extract, stannous fluoride, tetra sodium pyrophosphate, mono fluoro phosphate, Opatint D&C Red 27, polyphosphates, such as sodium hexametaphosphate, and cetylpyridinium chloride.

The denture cleansing compositions of the invention can be in paste, tablet, granular or powder form, although tablet-form compositions are highly preferred herein. Compositions in tablet form can be single or multiple layered tablets.

The following Examples further describe and demonstrate the preferred embodiments within the scope of the present invention.

EXAMPLES I TO V

The following are representative denture cleansing tablets according to the invention. The percentages are by weight of the total tablet. The tablets are made by compressing a mixture of the granulated components in a punch and dye tabletting press at a pressure of about $10^5$ kPa.

|  | I | II | III | IV | V |
|---|---|---|---|---|---|
| Malic Acid | 12 | 10 | 12 | — | 14 |
| Citric Acid | — | 10 | — | 12 | — |
| Sodium Carbonate | 10 | 8 | 8 | 6 | 10 |
| Sulphamic Acid | 5 | — | — | 3 | 3 |
| PEG 20,000 | — | 3 | 5 | 4 | 5 |
| PVP 40,000 | 5 | 3 | — | — | — |
| Sodium Bicarbonate | 21 | 23.2 | 23.9 | 13.9 | 20 |
| Sodium Perborate Monohydrate | 15 | 12 | 13 | 27 | 14 |
| Potassium Monopersulphate | 14.4 | 16 | 11 | — | 13.5 |
| Pyrogenic Silica | 0 | 0.3 | 0.1 | 0.1 | — |
| Talc | 2 | — | — | — | — |
| EDTA | — | — | 1 | — | 3 |
| EDTMP[1] | 1 | — | — | 1 | — |
| Flavor[4] | 2 | 1 | 2 | 1 | 2 |
| Polybutene | 0.6 | 1.5 | 5 | 8 | 0.5 |
| Silwet L7600[5] | 3 | 4 | — | 12 | 5 |
| Silwet L7230[6] | — | — | 9 | — | — |
| Bleach Precursor Agglomerate |  |  |  |  |  |
| TAED[2] | 2 | — | 4 | 5 | 2.5 |
| TMHOS[3] | 2 | 3 | — | — | — |
| Sulphamic Acid | 2 | 2 | 2 | 2 | 3.5 |
| Sodium Bicarbonate | 0.5 | 0.2 | 0.2 | 0.5 | 2 |
| PEG 6000 | 2.5 | 2 | 2.4 | 2.5 | 1.5 |
| Dye | — | 0.8 | 1.4 | 2 | 0.5 |
| Total | 100 | 100 | 100 | 100 | 100 |

[1]Ethylenediaminetetramethylenephosphonic acid
[2]Tetraacetylethylene diamine
[3]Sodium 3,5,5-trimethylhexanoyloxybenzene sulfonate
[4]Peppermint-based flavor
[5]CAS Registry No. 68938-54-5 from Union Carbide
[6]CAS Registry No. 68937-55-3 from Union Carbide In Examples I to V above, the overall tablet weight is 3 g; diameter 25 mm. The polybutene of Examples I to V is Indopol H-40, MW=750, trade name of BP Amoco Chemicals (Chicago, Ill.). The denture cleansing tablets of Examples I to V display improved antiplaque, cleansing and anti-bacterial activity together with excellent cohesion and other physical and in-use performance characteristics.

EXAMPLES VI TO VIII

The following are representative denture cleansing pastes according to the invention. The percentages are by weight of total composition.

|  | VI | VII | VIII |
|---|---|---|---|
| Calcium Carbonate | 20 | 25 | 15 |
| Glycerine | 10 | 12 | 8 |
| Sodium CMC | 3.5 | 3 | 4 |
| Titanium Dioxide | 0.7 | 0.5 | 0.6 |
| Methyl/Propyl Parabens | 0.1 | 0.1 | 0.1 |
| Sodium Saccharin | 0.3 | 0.4 | 0.2 |
| Flavor[4] | 1 | 1 | 2 |
| Polybutene | 1 | 1.5 | 0.3 |
| Silwet L7600[5] | 3 | 2.5 | 2 |
| Triclosan | — | 0.5 | — |
| Water | To 100% |  |  |

The polybutene of Examples VI to VIII is Indopol H-300, MW=1330, trade name of BP Amoco Chemicals (Chicago, Ill.). The denture cleansing pastes of Examples VI to VIII display improved antiplaque, flavor impact and anti-bacterial activity together with excellent cleansing characteristics.

The dentures or artificial teeth that are treated with the denture cleanser compositions described above should be exposed to the denture cleanser composition for a period of about 10 seconds to several hours, as in overnight treatment.

It is understood that the examples and embodiments described herein are for illustrative purposes only and that various modifications or changes in light thereof will be suggested to one of skill in the art without departing from the scope of the present invention.

What is claimed:

1. An effervescent denture cleanser composition in granule or tablet form comprising:
    a. polybutene with a molecular weight of about 300 to about 3000, said polybutene being a non-mucoadhesive flowable liquid that does not exhibit elastic, elastomeric, or rubbery behavior or properties and is not cross-linked;
    b. an inorganic persalt bleaching agent; and
    c. an effervescence generator.

2. The denture cleanser composition of claim 1 wherein the inorganic persalt bleaching agent comprises one or more bleaching agents selected from the group consisting of alkali metal persulfates, alkali metal perborates and mixtures thereof.

3. The denture cleansing composition of claim 1 wherein the effervescence generator comprises a (bi)carbonate/acid effervescent couple.

4. The denture cleanser composition of claim 1 further comprising a peroxyacid bleach precursor.

5. The denture cleanser composition of claim 4 wherein the organic peroxyacid precursor is selected from the group consisting of acylated polyalkyldiamines and carboxylic esters having the general formula AcL wherein Ac is the acyl moiety or an organic carboxylic acid comprising an optionally substituted, linear or branched C6–C20 alkyl or alkenyl moiety or a C6–C20 alkyl-substituted aryl moiety and L is a leaving group, the conjugate acid of which has a pKa in the range of 4 to 13.

6. The denture cleanser composition of claim 5 wherein the organic peroxyacid precursor is tetraacetylethylenediamine.

7. The denture cleanser composition of claim 1 further comprising a dental abrasive.

8. The denture cleanser composition of claim 7 wherein the dental abrasive is at a level from about 10% to about 70% by weight and is selected from the group consisting of silica, alumina, aluminosilicates, magnesium and zirconium silicates, calcium ortho-, pyro- meta- and polyphosphates, calcium and magnesium carbonates, insoluble metaphosphates and thermosetting polymerized resins.

9. The denture cleanser composition according to claim 1 further comprising a binder.

10. The denture cleanser composition according to claim 9 wherein the binder is present at a level of from about 0.1% to about 10%, by weight.

11. The denture cleanser composition according to claim 1 further comprising a chelating agent.

12. The denture cleanser composition according to claim 1 further comprising a lipophilic compound.

13. The denture cleanser composition of claim 12 wherein the lipophilic compound comprises a flavorant comprising one or more flavor components selected from the group consisting of wintergreen oil, oregano oil, bay leaf oil, peppermint oil, spearmint oil, clove oil, sage oil, sassafras oil, lemon oil, orange oil, anise oil, benzaldehyde, bitter almond oil, camphor, cedar leaf oil, marjoram oil, citronella oil, lavender oil, mustard oil, pine oil, pine needle oil, rosemary oil, thyme oil, cinnamon leaf oil, and mixtures thereof.

14. The denture cleanser composition of claim 13 wherein the lipophilic compound comprises antimicrobial compound selected from thymol, menthol, triclosan, 4-hexylresorcinol, phenol, methyl paraben, eucalyptol, benzoic acid, benzoyl peroxide, butyl paraben, methyl paraben, propyl paraben, salicylamides, and mixtures thereof.

15. The denture cleanser composition of claim 1 further comprising a surfactant.

16. The denture cleanser composition of claim 15 wherein the surfactant is a silicone surfactant selected from dimethicone copolyols, of the general formula (I)

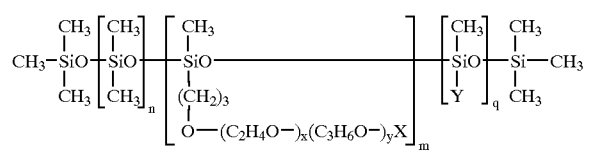

(I)

wherein X is selected from hydrogen, alkyl, alkoxy and acyl groups having from about 1 to about 16 carbon atoms, Y is $CH_3$, q is 0, n is from about 1 to about 100, m is from about 1 to about 40, the molecular weight of the residue $(C_2H_4O-)_x-(C_3H_6O-)_yX$ is from about 50 to about 2000, and x and y are such that the weight ratio of oxyethylene:oxypropylene is from about 100:0 to about 0:100.

17. The denture cleanser composition of claim 16 wherein the surfactant is a dimethicone copolyol, of the general formula (I) wherein the end-capping group X is methyl and y is 0, and mixtures thereof.

18. The denture cleanser composition of claim 1, wherein the polybutene has a molecular weight of from about 500 to about 2200.

19. The denture cleanser composition of claim 1, wherein the polybutene has a molecular weight of from about 750 to about 1500.

20. The denture cleanser of claim 1 further comprising one or more denture care active agents selected from the croup consisting of anti-calculus agents, fluoride ions sources, stannous ion sources, additional whitening agents, anti-microbial and anti-plaque agents, anti-inflammatory agents, nutrients, antioxidants, anti-viral agents, anti-fungal agents, analgesic and anesthetic agents, H-2 antagonists, components other than polybutene which impart a clean feel to the dentures, pigments and colorants, and mixtures thereof.

21. The denture cleanser of claim 20 wherein the denture care active is selected from the group consisting of triclosan, baking soda, sodium fluoride, potassium nitrate, sodium nitrate, nystatin, grapefruit seed extract, stannous fluoride, tetra sodium pyrophosphate, mono fluoro phosphate, Opatint D&C Red 27, polyphosphates, and cetylpyridium chloride.

22. The denture cleanser of claim 20 wherein the polyphosphate is sodium hexametaphosphate.

23. The denture cleanser composition of claim 20 wherein the fluoride ion source, if present, is in an amount sufficient to provide from about 50 ppm to about 3500 ppm of fluoride ions.

* * * * *